US009841379B2

(12) United States Patent
Bogaki et al.

(10) Patent No.: US 9,841,379 B2
(45) Date of Patent: Dec. 12, 2017

(54) FLUORESCENCE AND PHOSPHORESCENCE DETECTING APPARATUS

(71) Applicant: GLORY LTD., Himeji-shi, Hyogo (JP)

(72) Inventors: Akira Bogaki, Himeji (JP); Takahiro Yanagiuchi, Himeji (JP); Takaaki Morimoto, Himeji (JP); Satoru Oshima, Himeji (JP)

(73) Assignee: GLORY LTD., Himeji-shi, Hyogo (JP)

( * ) Notice: Subject to any disclaimer, the term of this patent is extended or adjusted under 35 U.S.C. 154(b) by 0 days.

(21) Appl. No.: 15/313,120

(22) PCT Filed: May 19, 2015

(86) PCT No.: PCT/JP2015/064354
§ 371 (c)(1),
(2) Date: Nov. 22, 2016

(87) PCT Pub. No.: WO2015/178384
PCT Pub. Date: Nov. 26, 2015

(65) Prior Publication Data
US 2017/0153184 A1     Jun. 1, 2017

(30) Foreign Application Priority Data

May 22, 2014  (JP) ................................ 2014-105859

(51) Int. Cl.
*F21V 9/16* (2006.01)
*G01N 21/64* (2006.01)
*G07D 7/121* (2016.01)

(52) U.S. Cl.
CPC ......... *G01N 21/6456* (2013.01); *G07D 7/121* (2013.01)

(58) Field of Classification Search
CPC .... G01J 1/58; G01N 21/6456; G01N 21/6408
(Continued)

(56) References Cited

U.S. PATENT DOCUMENTS

2014/0097359 A1 *  4/2014  Vasic ................. G01N 21/6408
                                                250/459.1
2015/0249104 A1    9/2015  Ota et al.

FOREIGN PATENT DOCUMENTS

JP    2004-355264 A    12/2004
JP    2007-72713 A      3/2007
(Continued)

*Primary Examiner* — David Porta
*Assistant Examiner* — Meenakshi Sahu
(74) *Attorney, Agent, or Firm* — Renner, Kenner, Greive, Bobak, Taylor & Weber

(57) ABSTRACT

To detect a fluorescent light and a phosphorescent light emitted from a paper sheet with a high precision, a fluorescence and phosphorescence detecting apparatus includes two sensor units. Each sensor unit includes a light source that emits an ultraviolet light on the paper sheet, an image sensor that captures images of the fluorescent light and the phosphorescent light excited on the paper sheet by irradiation of the ultraviolet light, and a light receiving lens that guides the fluorescent light and the phosphorescent light excited on the paper sheet to the image sensor. The two sensor units are arranged above and below the transport path and opposing each other across the transport path, and the light receiving lenses and the image sensors in the two sensor units are off-set along a transport direction of the paper sheet.

12 Claims, 7 Drawing Sheets

(58) Field of Classification Search
USPC .......................................... 250/458.1, 459.1
See application file for complete search history.

(56) References Cited

FOREIGN PATENT DOCUMENTS

| | | |
|---|---|---|
| JP | 3892081 B2 | 3/2007 |
| JP | 2010-39897 A | 2/2010 |
| JP | 2012-190253 | 10/2012 |
| WO | WO 99/09382 | 2/1999 |

\* cited by examiner

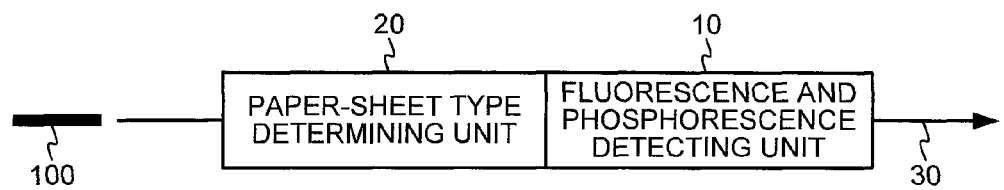
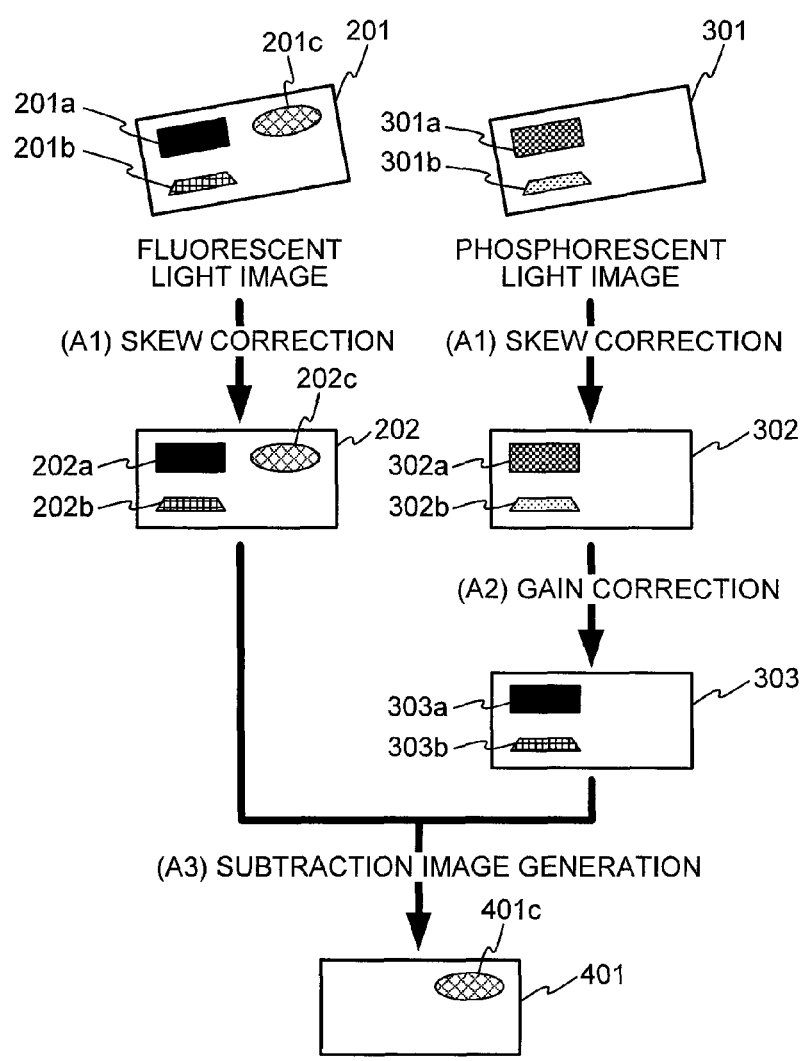

|  |  | AREA 1 | AREA 2 | ⋯ | AREA n |
|---|---|---|---|---|---|
| TYPE 1 | DIRECTION A | $\alpha 11$ | $\alpha 12$ | ⋯ |  |
|  | DIRECTION B |  |  |  |  |
|  | DIRECTION C |  |  |  |  |
|  | DIRECTION D |  |  |  |  |
| TYPE 2 | DIRECTION A | $\alpha 51$ | $\alpha 52$ | ⋯ |  |
|  | DIRECTION B |  |  |  |  |
|  | DIRECTION C |  |  |  |  |
|  | DIRECTION D |  |  |  |  |
| ⋮ |  |  |  |  |  |

FLUORESCENCE AND PHOSPHORESCENCE DETECTING APPARATUS

TECHNICAL FIELD

The present invention relates to a fluorescence and phosphorescence detecting apparatus that detects a fluorescent light and a phosphorescent light excited on a paper sheet.

BACKGROUND ART

A technique for determining an authenticity of a paper sheet based on optical characteristics of the paper sheet has been used in the art. For example, Patent Document 1 discloses an apparatus that detects reflection characteristics and transmission characteristics of a banknote. In this apparatus, two detecting units are arranged opposite to each other across a transport path of the banknote to perform authentication of a paper sheet. Each of the detecting units includes a light emitting unit that emits a light toward the banknote and a detecting sensor. The light is emitted toward the banknote from the light emitting unit of one of the detecting units, a reflected light reflected from the banknote is detected in one detecting unit, and a transmitted light that has passed through the banknote is detected in the other detecting unit. The two detecting units are arranged symmetrically in vertical direction. A reflection image of a front side of the banknote, a reflection image of a backside of the banknote, and a transmission image of the banknote can be acquired by making the two detecting units cooperate. In this apparatus, the light to be emitted can be selected among a visible light, an infrared light, and an ultraviolet light. Therefore, the authenticity of the banknote can be determined by acquiring a feature amount that appears in the reflection image and the transmission image of the banknote depending on the emitted light.

Patent Document 2 discloses an apparatus that emits two types of ultraviolet lights from light sources on a banknote that is being transported on a transport path of the banknote. A light receiving unit in the apparatus receives fluorescent light excited on the banknote because of the light emission. The apparatus acquires a feature amount relating to reflectance characteristics of the banknote corresponding to each of the emitted lights. Two pairs of the light source and the light receiving unit are arranged in this apparatus. Lights having different wavelengths are simultaneously emitted from the light sources, and a reflected light is detected in a corresponding one of the light receiving units thereby acquiring the feature amounts relating to the two types of the emitted lights. Moreover, Patent Document 2 also discloses an apparatus that includes two light sources corresponding to one light receiving unit, and that emits lights having different wavelengths from the light sources but at different timings thereby acquiring the feature amounts relating to the two types of ultraviolet lights.

Among the paper sheets such as a banknote, valuable securities, there are paper sheets in which a technology for preventing counterfeiting thereof, for example, such as a watermark, a hologram, a security thread has been used. Moreover, a paper sheet that is printed with an ink containing fluorescent material or phosphorescent material to prevent counterfeiting thereof is known in the art. When the fluorescent material and the phosphorescent material on the paper sheet are irradiated with an excitation light of a predetermined wavelength band, a fluorescent light and a phosphorescent light are excited. The fluorescent light disappears as soon as the irradiation of the excitation light is stopped; however, the phosphorescent light is emitted for awhile even after stopping the irradiation of the excitation light. The authenticity of the paper sheet can be determined from such a feature relating to an emission characteristic.

Patent Document 3 discloses an apparatus that observes a fluorescent light and a phosphorescent light for determining an authenticity of a paper sheet. In this apparatus, an excitation light of a predetermined wavelength band is emitted on a paper sheet that is placed on a workbench, and the authenticity of the banknote is determined from the observed phosphorescent light. Similarly, Patent Document 4 discloses an apparatus that acquires feature amounts relating to a fluorescent light and a phosphorescent light from a paper sheet. In this apparatus, two line image sensors are arranged at positions shifted in a transport direction of the paper sheet. The fluorescent light is detected with the line image sensor on the upstream side, and the phosphorescent light is detected with the line image sensor on the downstream side.

CITATION LIST

Patent Document

Patent Document 1: Japanese Patent Application Laid-Open No. 2004-355264
Patent Document 2: Japanese Patent No. 3892081
Patent Document 3: Japanese Patent Application Laid-Open No. 2007-072713
Patent Document 4: Japanese Patent Application Laid-Open No. 2010-039897

SUMMARY OF INVENTION

Technical Problem

However, conventionally, it was not possible to realize a compact apparatus that can detect with a high precision a phosphorescent light of a paper sheet transported at a high speed. Specifically, in the technique disclosed in Patent Document 4, because two sensors, one sensor for detecting the fluorescent light and one sensor for detecting the phosphorescent light, are necessary, it leads to increase in size of the apparatus. Moreover, because the technique disclosed in Patent Document 3 is intended for visual inspection of the fluorescent light and the phosphorescent light excited on the banknote that is stationary on the workbench, it cannot be applied as is to a paper sheet that is transported at a high speed.

Moreover, the techniques disclosed in Patent Documents 1 and 2 are intended for acquisition of the visible light image of the paper sheet, detection of the fluorescent light, and the like, so that it does not have a configuration for detection of a phosphorescent light. Accordingly, it is difficult to detect with a high precision the phosphorescent light that continues to emit even after stopping the irradiation of the excitation light, gradually weakens, and finally disappears. Particularly, it is difficult to detect with a high precision the phosphorescent light, which has weak emission intensity, excited on a paper sheet that is transported at a high speed. Thus, there is a need of an apparatus that can detect with a high precision a phosphorescent light excited on a paper sheet.

The present invention has been made in order to solve the above problems in the conventional technology. It is one object of the present invention to provide a fluorescence and phosphorescence detecting apparatus that can detect with a high precision a fluorescent light and a phosphorescent light excited on a paper sheet that is transported at a high speed.

Means for Solving Problems

To solve the above problem, and to achieve the above object, a fluorescence and phosphorescence detecting apparatus according to one aspect of the present invention, which detects a fluorescent light and a phosphorescent light emitted from a paper sheet that is transported on a transport path, includes two sensor units. Each of the two sensor units includes a light source that emits an ultraviolet light on the paper sheet; an image sensor that captures images of the fluorescent light and the phosphorescent light excited on the paper sheet by irradiation of the ultraviolet light; and a light receiving lens that guides the fluorescent light and the phosphorescent light excited on the paper sheet to the image sensor. The two sensor units are arranged above and below the transport path and opposing each other across the transport path, and the light receiving lenses and the image sensors in the two sensor units are off-set along a transport direction of the paper sheet.

In the above fluorescence and phosphorescence detecting apparatus, the sensor unit further includes a visible light cut-off filter arranged between the light source and the transport path; and an ultraviolet light cut-off filter arranged between the transport path and the image sensor, and the image sensor obtains a color image.

In the above fluorescence and phosphorescence detecting apparatus, the sensor unit further includes an image processing unit that corrects a gain of a phosphorescence image obtained by capturing the phosphorescent light by the image sensor, by using a coefficient set previously.

In the above fluorescence and phosphorescence detecting apparatus, the coefficient is a reciprocal number of a decay rate of the phosphorescent light.

In the above fluorescence and phosphorescence detecting apparatus, the coefficient is respectively set for each type and for each direction of the paper sheet.

In the above fluorescence and phosphorescence detecting apparatus, the coefficient is respectively set for each area of the paper sheet from which the phosphorescent light is excited.

In the above fluorescence and phosphorescence detecting apparatus, the coefficient is respectively set for each color of the phosphorescent light.

In the above fluorescence and phosphorescence detecting apparatus, the image processing unit generates a subtraction image from a gain corrected phosphorescence image and a fluorescence image obtained by capturing the fluorescent light by the image sensor.

In the above fluorescence and phosphorescence detecting apparatus, the image processing unit corrects the gain of the phosphorescence image to generate the subtraction image, the subtraction image is generated by removing an image of an area in which both the fluorescent light and the phosphorescent light are excited.

In the above fluorescence and phosphorescence detecting apparatus, the image sensor can acquire image data of the fluorescent light and the phosphorescent light at a pitch between 0.5 mm and 3.0 mm.

Advantageous Effects of Invention

According to the present invention, because the light receiving lens and the image sensor are arranged in an off-set manner in the transport direction in the two sensor units that are arranged opposing each other across the transport path on which a paper sheet is transported, even if the light sources in the two sensor units are turned on simultaneously, one light source is not affected by the light emitted from the opposing other light source. Therefore, the fluorescent light and the phosphorescent light can be detected with a high precision from both the front side and the back side of the paper sheet.

Moreover, according to the present invention, because the gain correction is performed on the image obtained by capturing the phosphorescent light having weak emission intensity, an image in which the area in which the phosphorescent light is captured appears clearly can be obtained.

Furthermore, according to the present invention, because the coefficient used in the gain correction of the phosphorescent light can be set previously, for example, for each area in which the phosphorescent light is excited, even if a plurality of different phosphorescent lights are excited on the paper sheet, the gain correction can be performed separately on the images obtained by capturing the phosphorescent lights, and the image in which all the areas from which the phosphorescent lights are captured appear clearly can be obtained.

BRIEF DESCRIPTION OF DRAWINGS

FIGS. 1A and 1B are schematic diagrams for explaining an outline of a processing performed in a fluorescence and phosphorescence detecting unit according to one present embodiment.

DESCRIPTION OF EMBODIMENTS

Figure 2:
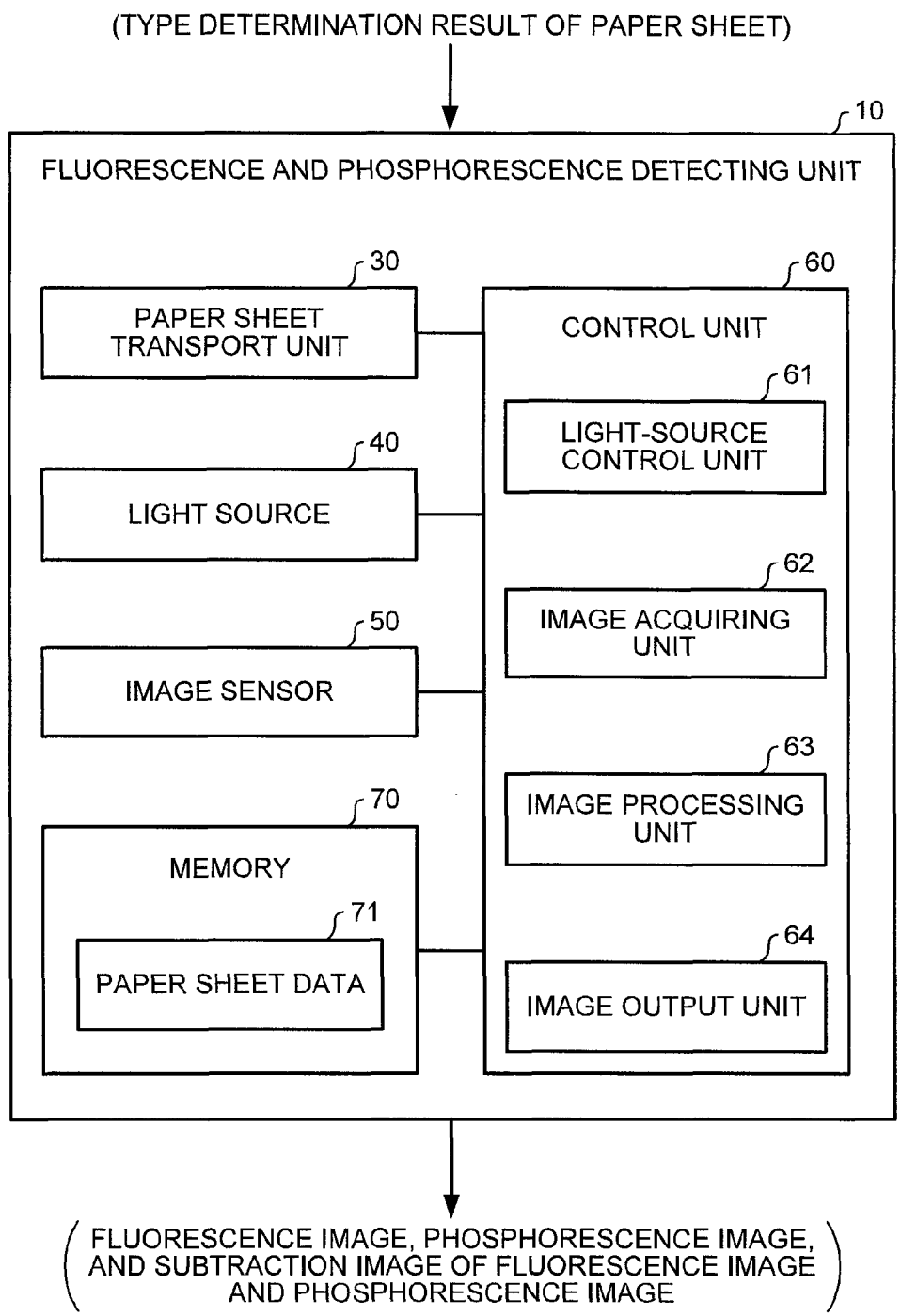
FIG. 2 is a schematic block diagram of a configuration of the fluorescence and phosphorescence detecting unit.

Exemplary embodiments of a fluorescence and phosphorescence detecting apparatus according to the present invention are explained below with reference to the accompanying drawings. The fluorescence and phosphorescence detecting apparatus is used, for example, in a paper sheet handling apparatus that determines a type, authenticity, and the like, of a paper sheet, and also counts the number and the like of the paper sheets. For example, the paper-sheet authentication apparatus, which determines the authenticity of the paper sheet in the paper sheet handling apparatus, determines the authenticity of the paper sheet based on a feature amount acquired from a visible light image that is obtained by capturing the paper sheet, and detection results of a fluorescent light and a phosphorescent light obtained in the fluorescence and phosphorescence detecting apparatus.

As long as the paper sheet is the one on which a fluorescent light and a phosphorescent light are excited when it is irradiated with an excitation light of a predetermined wavelength band, the type of the paper sheet as a processing object for detecting the fluorescence and the phosphorescence is not particularly limited. For example, such a processing object includes a coupon, a gift certificate, a stock certificate, a check, a banknote, and the like.

At first, an outline of a processing performed in a fluorescence and phosphorescence detecting unit (the fluorescence and phosphorescence detecting apparatus) according to the present embodiment is explained. FIGS. 1A and 1B are schematic diagrams for explaining an outline of processing performed in a fluorescence and phosphorescence detecting unit 10. As shown in FIG. 1A, the fluorescence and phosphorescence detecting unit 10 is connected to a paper-sheet type determining unit 20. A paper sheet 100 transported on a transport path in a paper sheet handling apparatus by a paper sheet transport unit 30 passes through the paper-sheet type determining unit 20 and the fluorescence and phosphorescence detecting unit 10. Moreover, in the paper sheet handling apparatus, a not-shown paper sheet authentication unit determines an authenticity of the paper sheet 100 based on a determination result obtained by the paper-sheet type determining unit 20, detection result of the fluorescence and detection result of the phosphorescence by the fluorescence and phosphorescence detecting unit 10, and detection results relating to magnetism, a thickness, and the like of the paper sheet, and the like.

The paper-sheet type determining unit 20 determines the type of the paper sheet 100 before the paper sheet 100 transported by the paper sheet transport unit 30 arrives at a detection position at which a fluorescent light and a phosphorescent light are detected by the fluorescence and phosphorescence detecting unit 10. The determination result obtained by the paper-sheet type determining unit 20 is inputted into the fluorescence and phosphorescence detecting unit 10. The type of the paper sheet 100 is information for identifying a type of a light excited on the paper sheet 100 and a position and a dimension of a partial area on the paper sheet 100 from which the light is excited. For example, when the paper sheet 100 is a banknote, denomination information determined by the paper-sheet type determining unit 20, and information about front side up/back side up and a transport direction are inputted into the fluorescence and phosphorescence detecting unit 10 as the type determination result. In FIG. 1A, the paper-sheet type determining unit 20 and the fluorescence and phosphorescence detecting unit 10 are arranged sequentially on the transport path; however, the fluorescence and phosphorescence detecting unit 10 can be included in the paper-sheet type determining unit 20.

In the fluorescence and phosphorescence detecting unit 10, information such as the type of the light excited on the paper sheet 100, the partial area on the paper sheet 100 that emits the light, and the like, are stored previously in association with the types of the paper sheets 100. The fluorescence and phosphorescence detecting unit 10, based on the information about the type of the paper sheet 100 received from the paper-sheet type determining unit 20, following a timing at which the paper sheet 100 is transported inside the unit, controls on/off timings of a light source that emits an excitation light on the paper sheet 100 and captures the fluorescent light and the phosphorescent light excited by the excitation light.

FIG. 1B shows examples of images acquired by capturing the fluorescent light and the phosphorescent light excited on the paper sheet 100 and a processing performed on each of the images. As shown in FIG. 1B, the fluorescence and phosphorescence detecting unit 10 acquires a fluorescence image 201 obtained by capturing the fluorescent light excited on the paper sheet 100 and a phosphorescence image 301 obtained by capturing the phosphorescent light excited on the paper sheet 100. The fluorescence image 201 includes fluorescence area images 201a to 201c that are three partial areas from which the fluorescent light is excited. The phosphorescence image 301 includes phosphorescence area images 301a and 301b that are two partial areas from which the phosphorescent light is excited.

The example of FIG. 1B shows that the phosphorescent light is excited and the phosphorescence area images 301a and 301b are acquired in the same partial areas on the paper sheet 100 in which the fluorescent light is excited and the fluorescence area images 201a and 201b are acquired. Therefore, the fluorescence area images 201a and 201b in the fluorescence image 201 and the phosphorescence area images 301a and 301b in the phosphorescence image 301 are the same areas. On the other hand, in the partial area from which the fluorescence area image 201c is acquired, only the fluorescent light is excited and the phosphorescent light is not excited. Therefore, in the phosphorescence image 301, no phosphorescence area image is acquired from the area that corresponds to the fluorescence area image 201c in the fluorescence image 201.

If the fluorescence image 201 and the phosphorescence image 301 are skewed because the paper sheet 100 is transported on the transport path in a skewed state, at first, the fluorescence and phosphorescence detecting unit 10 corrects the skew of the images (A1). Subsequently, the fluorescence and phosphorescence detecting unit 10 corrects a gain of each of phosphorescence area images 302a and 302b so that the phosphorescence area images 302a and 302b clearly appear on a skew-corrected phosphorescence image 302 (A2). Specifically, a pixel value of each of the pixels forming the phosphorescence area images 302a and 302b is converted by multiplying by a coefficient set previously. The coefficient is set previously for each area from which the phosphorescent light is emitted. The coefficients are stored in the fluorescence and phosphorescence detecting unit 10 for each type of the paper sheet 100 and for each area. Instead of setting the coefficient for each area, for example, it is allowable to set the coefficient depending on the color of the fluorescent light and the phosphorescent light.

Each of the coefficients used to correct the gain of the phosphorescence area images 302a and 302b is set such that a pixel value obtained by multiplying a pixel value of each of the pixels forming the phosphorescence area images 302a and 302b with the coefficient is approximately equal to a pixel value of each of the pixels forming corresponding fluorescence area images 202a and 202b. For example, a reciprocal number of a decay rate of the phosphorescent light, or a value depending on this reciprocal number, is set as the coefficient. Different coefficients can be set in the phosphorescence area image 302a and the phosphorescence area image 302b. In a gain-corrected phosphorescence image 303 obtained by using thus set coefficient, a pixel value of each of the pixels forming a phosphorescence area image 303a is approximately equal to a pixel value of the corresponding pixel that is one of the pixels forming the fluorescence area image 202a in a fluorescence image 202. Similarly, corresponding pixels of a gain-corrected phosphorescence area image 303b and the fluorescence area image 202b have approximately the same pixel values.

After completing the gain correction of each of the phosphorescence area images 302a and 302b included in the phosphorescence image 302, the fluorescence and phosphorescence detecting unit 10 generates a subtraction image by subtracting the pixel value of each of the pixels forming the gain-corrected phosphorescence image 303 from the pixel value of each of the pixels forming the fluorescence image 202 (A3). As a result, a subtraction image 401 is obtained that contains only a fluorescence area image 401c because the fluorescence area images 202a and 202b corresponding to the phosphorescence area images 303a and 303b of the phosphorescence image 302 are removed from the fluorescence image 202.

In this manner, the subtraction image does not contain a partial area image of a captured light in the area in which both the fluorescent light and the phosphorescent light are captured; however, contains a partial area image of the area in which only the fluorescent light is captured and a partial area image of the area in which only the phosphorescent light is captured.

Because the emission intensity of the phosphorescent light is weak, it may be difficult to check the phosphorescence area images 302a and 302b on the phosphorescence image 302. Even in this case, because the fluorescence and phosphorescence detecting unit 10 performs the gain correction by using the coefficient set previously depending on the emission intensity of the phosphorescent light for each area from which the phosphorescent light is excited, clear phosphorescence area images 303a and 303b can be obtained.

The emitting state of the fluorescent light and the phosphorescent light changes depending on the state of the paper sheet 100 such as a stain or a secular change of the paper sheet 100. Accordingly, depending on the state of the paper sheet 100, different images may be obtained even if the same light from the same paper sheet 100 is captured. Even in this case, in the fluorescence and phosphorescence detecting unit 10, the subtraction image 401 is obtained from the fluorescence image 202 and the gain-corrected phosphorescence image 303, and therefore any effect of the state of the paper sheet 100 can be suppressed.

When the fluorescence images 201 and 202, the phosphorescence images 301 to 303, and the subtraction image 401 are obtained, the fluorescence and phosphorescence detecting unit 10 determines the authenticity of the paper sheet 100 by using these images. For example, an image obtained by the fluorescence and phosphorescence detecting unit 10 by using a genuine paper sheet 100 can be prepared previously as a template image, and the authenticity of the paper sheet 100 can be determined based on a comparative evaluation between the template image and the actual image obtained by the fluorescence and phosphorescence detecting unit 10. The authentication of the paper sheet 100 can be performed by using this evaluation result by the paper sheet authentication unit connected to the paper-sheet type determining unit 20 and the fluorescence and phosphorescence detecting unit 10. Which image(s) among the fluorescence images 201 and 202, the phosphorescence images 301 to 303, and the subtraction image 401 obtained by the fluorescence and phosphorescence detecting unit 10 is to be used when performing the authentication of the paper sheet 100 is appropriately set depending on the type of the paper sheet 100 and the functions available in the paper sheet authentication unit.

Subsequently, a configuration of the fluorescence and phosphorescence detecting unit 10 is explained. FIG. 2 is a schematic block diagram of the configuration of the fluorescence and phosphorescence detecting unit 10. The fluorescence and phosphorescence detecting unit 10, as shown in FIG. 1, has a function to acquire a type determination result of the paper sheet 100 from the paper-sheet type determining unit 20, and output at least one among the fluorescence images 201 and 202, the phosphorescence images 301 to 303, and the subtraction image 401 of the fluorescence image and the phosphorescence image depending on the type of the paper sheet 100. The image outputted from the fluorescence and phosphorescence detecting unit 10 is inputted into an external device such as the paper sheet authentication unit.

The fluorescence and phosphorescence detecting unit 10 includes the paper sheet transport unit 30, a light source 40, an image sensor 50, a control unit 60, and a memory 70. The paper sheet transport unit 30 has a function to transport the paper sheet 100 on the transport path in the fluorescence and phosphorescence detecting unit 10. The paper sheet transport unit 30 transports the paper sheet 100 at a high speed of 2000 mm/s, for example. The light source 40 has a function to emit, by using a light emitting element such as an LED, a light of a predetermined wavelength band on the paper sheet 100 that is transported on the transport path by the paper sheet transport unit 30. The light source 40 emits an ultraviolet light on the paper sheet 100 by using an ultraviolet LED, for example. The light source 40 can have a configuration in which the light emitted by the LED directly falls on the paper sheet 100, or can have a configuration in which the light emitted by the LED falls on the paper sheet 100 via a light guide.

The image sensor 50 has a function to acquire the image of the fluorescent light and the image of the phosphorescent light that are excited on the paper sheet 100. The image sensor 50 is constituted by light receiving elements, such as photodiodes, and RGB color filters. Specifically, for example, a plurality of light receiving elements each having a light receiving surface of 26 μm×45 μm (main-scanning direction×sub-scanning direction) is arranged in a row in the main-scanning direction with a center-to-center distance of 42.3 μm. Three rows are arranged side-by-side with a center-to-center distance of 84.6 μm in the sub-scanning direction. Moreover, the RGB color filters are arranged so that an R (red) color filter is installed on the light receiving elements of a first row, a G (green) color filter is installed on the light receiving elements of a second row, and a B (blue) color filter is installed on the light receiving elements of a third row. As a result, color images of each of the RGB colors and a full-color image can be acquired in the image sensor 50. The installation position of the image sensor 50 is adjusted so that the direction of the row in which the light receiving elements are arranged is orthogonal to the transport direction of the paper sheet transport unit 30. Therefore, because line data of each of the RGB colors can be acquired by scanning line-by-line the paper sheet 100 that is transported by the paper sheet transport unit 30, the image data of each of the RGB colors of the entire paper sheet 100 and the image data of full color of the entire paper sheet 100 can be acquired.

The memory 70 is a nonvolatile storage device such as semiconductor memory or a hard disk, and paper sheet data 71 is stored therein. For example, information about a partial area from which the fluorescent light is excited on the paper sheet 100, information about a partial area from which the phosphorescent light is excited, information about a coefficient used in the gain correction of the phosphorescence image 302, information about capturing conditions used when acquiring the fluorescence image 201 and the phosphorescence image 301, and the like are stored in the memory 70 for every type of the paper sheet 100.

The control unit 60 includes a light-source control unit 61, an image acquiring unit 62, an image processing unit 63, and an image output unit 64. The light-source control unit 61 controls the light source 40 used to acquire the fluorescence image 201 and the phosphorescence image 301. The image acquiring unit 62 includes a function to acquire the fluorescence image 201 and the phosphorescence image 301 of the paper sheet 100 transported by the paper sheet transport unit 30. The details relating to an acquisition method of the fluorescence image 201 and the phosphorescence image 301 by the light-source control unit 61 and the image acquiring unit 62 will be explained later.

The image processing unit 63 has a function to perform processing such as skew correction of the fluorescence image 201 and the phosphorescence image 301 that are acquired by the image acquiring unit 62, gain correction of the phosphorescence image 302, and generation of the subtraction image 401 from the fluorescence image 202 and the phosphorescence image 303.

Figures 3A, 3B:
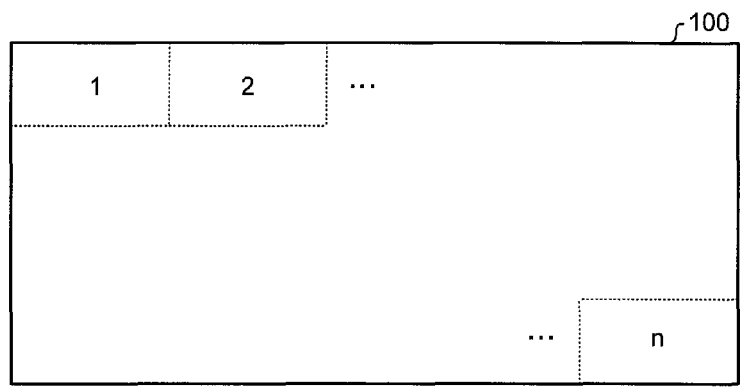
FIGS. 3A and 3B are schematic diagrams for explaining a coefficient table used in gain correction of a phosphorescence image.

The gain correction of the phosphorescence image 302 by the image processing unit 63 is performed by using a coefficient table for gain correction. The coefficient table is included in the paper sheet data 71 that has been stored in the memory 70. FIGS. 3A and 3B are schematic diagrams for explaining the coefficient table to be used in the gain correction of the phosphorescence image 302. As shown in FIG. 3A, the paper sheet 100 is divided in partial areas 1 to n based on the area in which the fluorescent light is excited and the area in which the phosphorescent light is excited on the paper sheet 100. In the coefficient table, a different coefficient can be set depending on the type of the paper sheet, a direction of the paper sheet 100 and the areas 1 to n on the paper sheet 100. When the paper sheet 100 shown in FIG. 3A has a portrait printed on a front side surface, the directions in the coefficient table are defined as below. When the paper sheet 100 is the front side up with the head of the portrait located in an upper part thereof, it is called direction "A". When the paper sheet 100 is the front side up with the head of the portrait located in a lower part thereof, it is called direction "B". When the paper sheet 100 is the back side up with the head of the portrait located in a lower part thereof, it is called direction "C". When the paper sheet 100 is the back side up with the head of the portrait located in an upper part thereof, it is called direction "D".

For example, when a type determination result of the paper sheet 100 indicating that the paper sheet 100 is of a type "1" with the direction "A" is inputted into the fluorescence and phosphorescence detecting unit 10 from the paper-sheet type determining unit 20, the image processing unit 63 refers to the coefficient table included in the paper sheet data 71 that has been stored in the memory 70. In the example of FIG. 3B, for example, in the area 1, the image processing unit 63 corrects a gain by multiplying a pixel value of each of the pixels with a coefficient all corresponding to the type 1 and the direction A. Also, in the area 2, the image processing unit 63 corrects the gain by multiplying a pixel value of each of the pixels with a coefficient α12 corresponding to the type 1 and the direction A.

The image output unit 64 has a function to output to the external device at least one among the fluorescence images 201 and 202, the phosphorescence images 301 to 303, and the subtraction image 401 acquired by the fluorescence and phosphorescence detecting unit 10. An image or images to output to the external device is previously set depending on the type of the paper sheet 100 and the external device that is the output destination. The image output unit 64 selects the image(s) based on this setting and outputs the image(s). For example, the image output unit 64 outputs the subtraction image 401 to the paper sheet authentication unit. The paper sheet authentication unit acquires, apart from the image received from the fluorescence and phosphorescence detecting unit 10 and the information about the type of the paper sheet 100 received from the paper-sheet type determining unit 20, data such as the visible light image, the magnetic characteristics, the thickness of the paper sheet 100. The paper sheet authentication unit analyzes the acquired data and determines the authenticity of the paper sheet 100.

Figure 4:
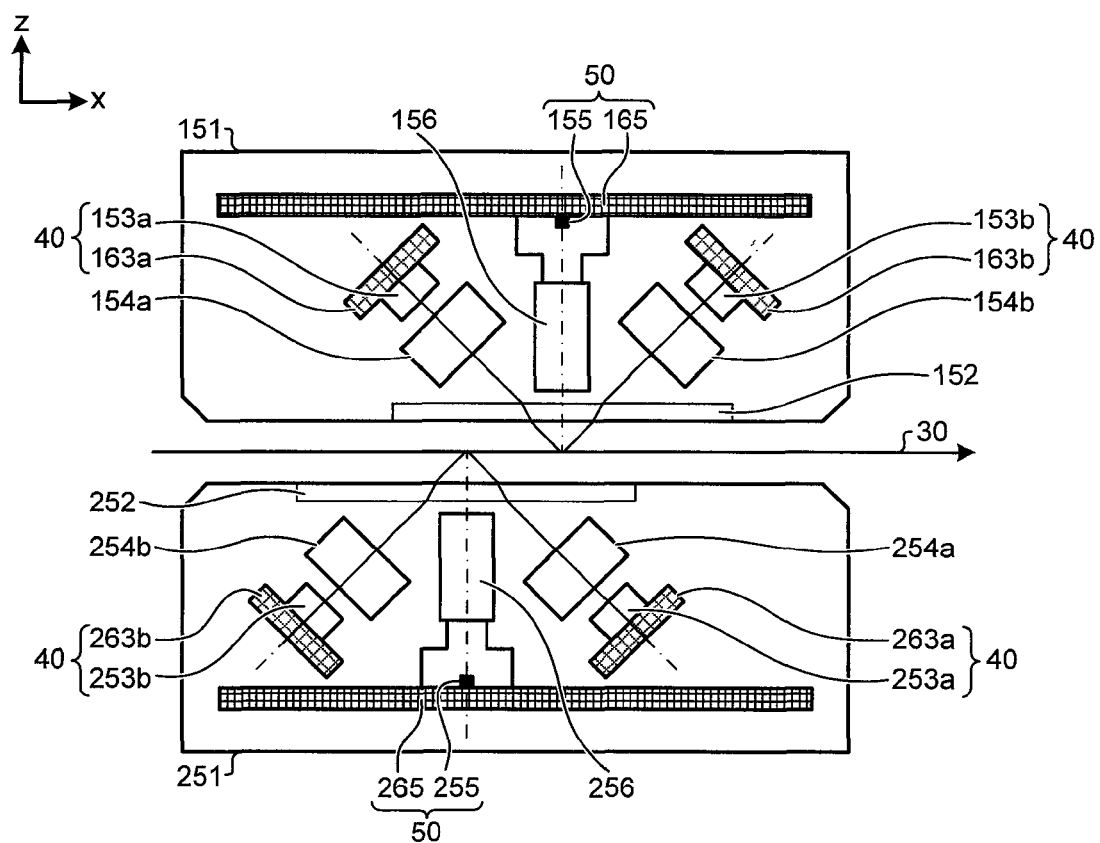
FIG. 4 is a schematic cross-sectional view of sensor units.

Subsequently, a structure of sensor units 151 and 251 that constitute the fluorescence and phosphorescence detecting unit 10 is explained. FIG. 4 is a schematic cross-sectional view showing the structure of the sensor units 151 and 251. FIG. 4 shows the cross-section of the sensor units 151 and 251 viewed from a side thereof. The positive X-axis direction in FIG. 4 corresponds to the transport direction to which the paper sheet 100 is transported by the paper sheet transport unit 30. In the fluorescence and phosphorescence detecting unit 10, the two sensor units 151 and 251 are arranged opposing each other across the transport path on which the paper sheet 100 is transported by the paper sheet transport unit 30.

The upper sensor unit 151 is explained now. The upper sensor unit 151 has a sensor case and a transparent member 152 fitted to a part of the sensor case. The light source 40, the image sensor 50, and the like are arranged in the sensor case.

The light source 40 includes, as shown in FIG. 4, an LED 153a on a left substrate 163a and an LED 153b on a right substrate 163b. Each of the LEDs 153a and 153b is an ultraviolet LED that emits an ultraviolet light. Visible light cut-off filters 154a and 154b are respectively arranged in a direction in which the ultraviolet lights are emitted from the LEDs 153a and 153b toward the paper sheet 100. These visible light cut-off filters 154a and 154b filter-out a visible light component having a wavelength of 400 nm or more from the lights emitted by the LEDs 153a and 153b. The ultraviolet light, emitted by each of the two LEDs 153a and 153b that has passed through the respective visible light cut-off filters 154a and 154b, passes through the transparent member 152 and is emitted toward the paper sheet 100 transported by the paper sheet transport unit 30. A pair of the LEDs 153a and 153b is shown in FIG. 4. However, a large number of LEDs constituting the light source 40 are arranged in a direction (Y-axis direction) orthogonal to the transport direction (X-axis direction). The LEDs constituting the light source 40 are arranged corresponding to the position of the image sensor 50 so that sufficient light is emitted on an entire area on the paper sheet 100 that is the target to be captured by the image sensor 50.

The image sensor 50 includes a light receiving element 155, such as a photodiode, that is fixed to a substrate 165, and an RGB color filter and the like to acquire color data by each of the light receiving elements 155. A rod lens array (a light receiving lens) 156 that receives light reflected from the paper sheet 100 is arranged on an optical path from the paper sheet transport unit 30 to the light receiving element 155. To be able to capture an entire upper surface of the paper sheet 100 transported by the paper sheet transport unit 30, the light receiving elements 155 that constitute the image sensor 50 are arranged in a row along a direction that is orthogonal to the transport direction. Rod lenses provided corresponding to every predetermined number of the light receiving elements 155 constitute the rod lens array 156. An ultraviolet light cut-off filter is deposited on each of the rod lenses. Accordingly, the ultraviolet light components of 400 nm or less are filtered out before the light from the paper sheet 100 reaches the light receiving element 155.

The light that is reflected from the upper surface of the paper sheet 100 transported by the paper sheet transport unit 30 and that has passed through the transparent member 152 enters into the rod lens array 156 from a lower surface thereof and is detected by the light receiving elements 155. Accordingly, the upper sensor unit 151 can capture the entire upper surface of the paper sheet 100 transported by the paper sheet transport unit 30.

In the lower sensor unit 251, in the same manner as the upper sensor unit 151, the light source 40 includes an LED 253a on a right substrate 263a and an LED 253b on a left substrate 263b. Each of the LEDs 253a and 253b is an ultraviolet LED that emits an ultraviolet light. Visible light cut-off filters 254a and 254b are respectively arranged in a direction in which the ultraviolet lights are emitted from the LEDs 253a and 253b toward the paper sheet 100. These visible light cut-off filters 254a and 254b filter-out a visible light component having a wavelength of 400 nm or more from the lights emitted by the LEDs 253a and 253b. Remaining light component passes through a transparent member 252 and is emitted toward the paper sheet 100 transported by the paper sheet transport unit 30. A pair of the LEDs 253a and 253b is shown in FIG. 4. However, a large number of LEDs constituting the light source 40 are arranged in a direction (Y-axis direction) orthogonal to the transport direction (X-axis direction). The LEDs constituting the light source 40 are arranged corresponding to the position of the image sensor 50 so that sufficient light is emitted on an entire area on the paper sheet 100 that is the target to be captured by the image sensor 50.

The lower sensor unit 251 includes the image sensor 50. The image sensor 50 includes a light receiving element 255, such as a photodiode, which is fixed to a substrate 265, and an RGB color filter and the like to acquire color data by each of the light receiving elements 255. A rod lens array (a light receiving lens) 256 is arranged on an optical path from the paper sheet transport unit 30 to the light receiving element 255. To be able to capture an entire back side of the paper sheet 100 transported by the paper sheet transport unit 30, the light receiving elements 255 that constitute the image sensor 50 are arranged in a row along a direction that is orthogonal to the transport direction. Rod lenses provided corresponding to every predetermined number of the light receiving elements 255 constitute the rod lens array 256. An ultraviolet light cut-off filter is deposited on each of the rod lenses. Accordingly, the ultraviolet light components of 400 nm or less are cut before the light from the paper sheet 100 reaches the light receiving element 255.

The light that is reflected from a lower surface of the paper sheet 100 transported by the paper sheet transport unit 30 and that has passed through the transparent member 252 enters into the rod lens array 256 from an upper surface thereof and is detected by the light receiving elements 255. Accordingly, the lower sensor unit 251 can capture the entire lower surface of the paper sheet 100 transported by the paper sheet transport unit 30.

As shown in FIG. 4, the upper sensor case of the sensor unit 151 and the lower sensor cases of the sensor unit 251 are arranged symmetrically above and below the transport path. This configuration allows a mounting base that supports each of the upper and lower sensors to be shared with other sensors. The mounting base can be used for a plurality of types of sensors. Therefore, instead of the sensor units 151 and 251, sensor units having other function, such as ultrasonic sensors, can be mounted facing each other by using the same mounting base. This configuration allows reduction in the cost of the mounting base for each of the sensor units.

As shown in FIG. 4, the sensor cases of the two sensor units 151 and 251 are arranged above and below and opposing each other across the transport path such that they are located at the same position in the X-axis direction. On the other hand, the rod lens array 156 and the light receiving element 155 in the sensor unit 151 installed above the transport path and the rod lens array 256 and the light receiving element 255 in the sensor unit 251 installed below the transport path are arranged at positions that are off-set along the transport direction (X-axis direction). With this arrangement, the upper sensor unit 151 can capture the entire upper surface of the paper sheet 100 without being affected by the light emitted from the lower sensor unit 251 toward the lower surface of the paper sheet 100. Similarly, the lower sensor unit 251 can capture the entire lower surface of the paper sheet 100 without being affected by the light emitted from the upper sensor unit 151 toward the upper surface of the paper sheet 100.

Figure 5:
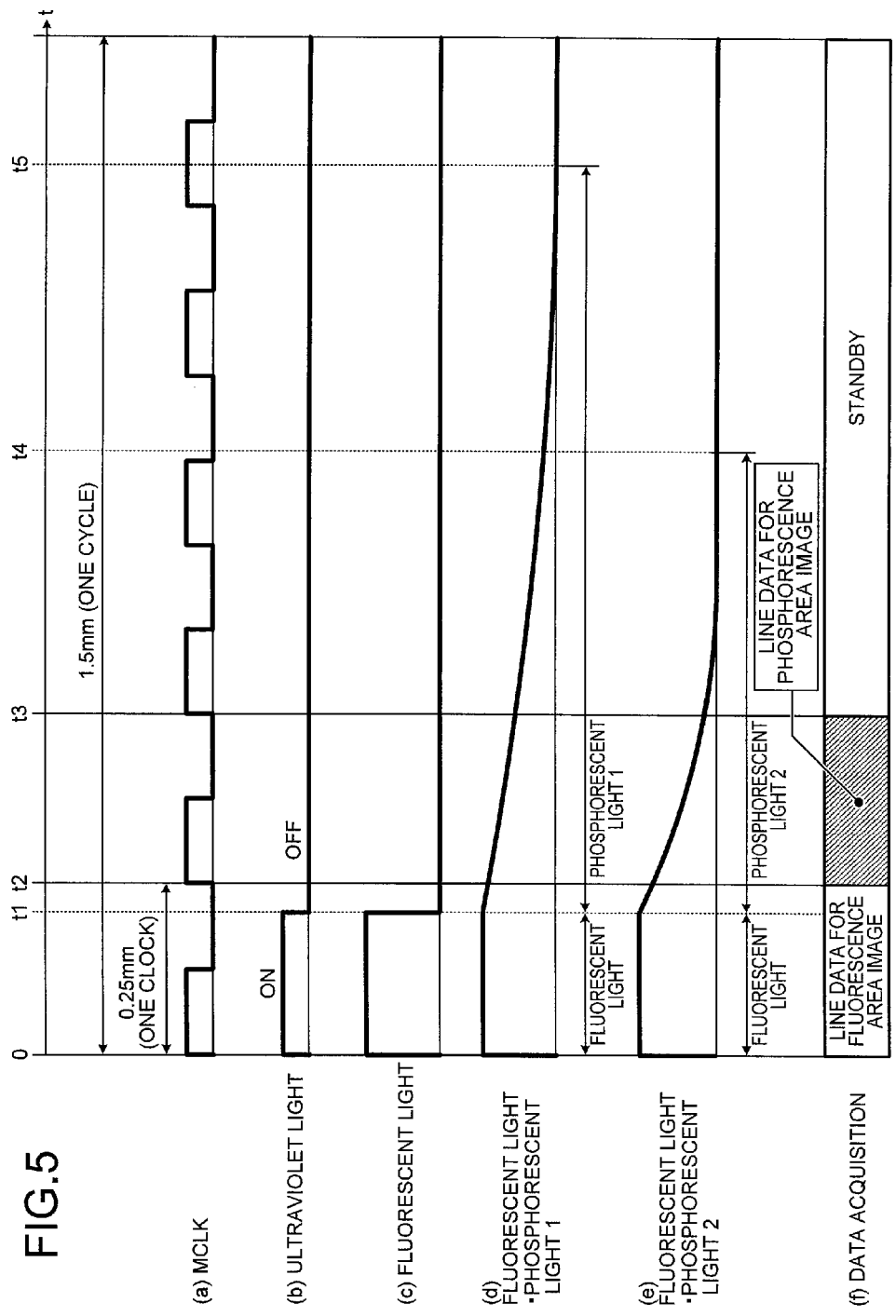
FIG. 5 is a timing chart for explaining a method of acquiring a fluorescence image and a phosphorescence image of a paper sheet implemented by the fluorescence and phosphorescence detecting unit.

Subsequently, a method of acquiring the fluorescence image and the phosphorescence image of the paper sheet 100 implemented by the fluorescence and phosphorescence detecting unit 10 will be explained. FIG. 5 shows a timing chart for explaining a method of acquiring the fluorescence image and the phosphorescence image of the paper sheet 100 implemented by the fluorescence and phosphorescence detecting unit 10. Because the same method is implemented in the upper sensor unit 151 and the lower sensor unit 251 of the fluorescence and phosphorescence detecting unit 10 when acquiring the fluorescence image and the phosphorescence image, the method implemented in the upper sensor unit 151 only is explained as an example. Moreover, in the following explanation, it is assumed that the paper sheet 100 is transported by the paper sheet transport unit 30 at a transport speed of 2000 mm/s.

A time axis is shown at the top in FIG. 5. A clock signal (MCLK) used in the operation of various parts of the fluorescence and phosphorescence detecting unit 10 is shown in (a) of FIG. 5. Moreover, (b) of FIG. 5 shows emission timings of the ultraviolet light emitted from the light source 40, and (c) to (e) of FIG. 5 show examples of the fluorescent light and the phosphorescent light excited on the paper sheet 100 by the ultraviolet light emitted from the light source 40. Moreover, (f) of FIG. 5 shows acquisition timings of line data to generate the fluorescence image and line data to generate the phosphorescence image. The time required to transport the paper sheet 100 for a distance of 1.5 mm is taken as one cycle. In this one cycle shown in FIG. 5, one line data for generating the fluorescence image and one line data for generating the phosphorescence image are acquired.

Specifically, based on a transport timing of the paper sheet 100 by the paper sheet transport unit 30, the light-source control unit 61 detects a timing at which a leading edge in the transport direction of a partial area (a fluorescence area) from which the fluorescent light is excited or of a partial area (a phosphorescence area) from which the phosphorescent light is excited on the paper sheet 100 has arrived within a measurement area by the image sensor 50. Upon detecting the arrival of the leading edge of the paper sheet 100, the light-source control unit 61 turns on the light source 40 (t=0, "ON" in (b) of FIG. 5). Moreover, the light-source control unit 61 turns off the light source 40 earlier than the time for one clock has elapsed, i.e., at a timing (t=t1) that is earlier than the time (t=t2) required to transport the paper sheet 100 for the distance of 0.25 mm ("OFF" in (b) of FIG. 5). Accordingly, the ultraviolet LEDs 153*a* and 153*b* of the light source 40 are turned on only during t=0 to t=t1, and the ultraviolet lights are emitted on the paper sheet 100 during this period.

The timings at which the fluorescence area and the phosphorescence area reach the measurement area by the image sensor 50 are calculated based on information about the transport timing by the paper sheet transport unit 30 and information about the fluorescence area and the phosphorescence area on the paper sheet 100 that are obtained by referring to the paper sheet data 71 stored in the memory 70 based on the type determination result of the paper sheet 100 inputted to the fluorescence and phosphorescence detecting unit 10. Moreover, a type of the light (wavelength band of the light) emitted from the light source 40, emission intensity of the emitted light, a timing of turning off the light source 40, and the like are set for each type of the paper sheet 100 and previously stored in the memory 70 as the paper sheet data 71, and the light source 40 is controlled based on this setting information.

An example of the paper sheet 100 including the fluorescence area is shown in (c) of FIG. 5. In (c) of FIG. 5, the vertical axis represents the emission intensity of the fluorescent light excited in the fluorescence area. In the fluorescence area, as shown in (c) of FIG. 5, the fluorescent light is excited at a timing (t=0) at which the light source 40 is turned on, and the fluorescent light disappears at a timing (t=t1) at which the light source 40 is turned off.

An example of the paper sheet 100 including the fluorescence area and the phosphorescence area is shown in (d) of FIG. 5. In (d) of FIG. 5, the vertical axis represents the emission intensities of the fluorescent light and the phosphorescent light. Unlike the fluorescent light, the emission intensity of the phosphorescent light gradually increases after the emission of the excitation light is started, and becomes saturated. The phosphorescent light continues for a while after the emission of the excitation light is stopped, but the emission intensity thereof is weakening. The phosphorescent light gradually decays, and finally disappears. Also in (d) of FIG. 5, like in (c) of FIG. 5, in the fluorescence area on the paper sheet 100, the fluorescent light is excited at a timing (t=0) at which the light source 40 is turned on, and the fluorescent light disappears at a timing at which the light source 40 is turned off. In addition, in (d) of FIG. 5, the phosphorescent light, which is excited in the phosphorescence area, continues even after turning off the light source 40. The phosphorescent light gradually decays from the timing (t=t1) at which the light source 40 is turned off, and then disappears (t=t5).

Another example of the paper sheet 100 including a fluorescence area and a phosphorescence area is shown in (e) of FIG. 5. The paper sheet 100 of this example is different from the one shown in (d) of FIG. 5. In (e) of FIG. 5, the vertical axis represents the emission intensities of the fluorescent light and the phosphorescent light. For example, the emission intensity of the phosphorescent light and the time until the phosphorescent light decays and disappears change depending on the type of the ink that emits the phosphorescent light, namely the type of the phosphorescence material. Also in (e) of FIG. 5, like in (c) of FIG. 5, in the fluorescence area on the paper sheet 100, the fluorescent light is excited at a timing (t=0) at which the light source 40 is turned on, and the fluorescent light disappears at a timing at which the light source 40 is turned off. In addition, in (e) of FIG. 5, like in (d) of FIG. 5, the phosphorescent light, which is excited in the phosphorescence area, continues even after turning off the light source 40. However, because the phosphorescence material in (e) of FIG. 5 is different from the phosphorescent material in (d) of FIG. 5, the phosphorescent light disappears at a timing (t=t4) that is earlier than the same in (d) of FIG. 5.

In the fluorescence and phosphorescence detecting unit 10, the image acquiring unit 62 acquires the line data to generate the fluorescence area image and the line data to generate the phosphorescence area image at timings shown in (f) of FIG. 5. The fluorescent light is excited in the fluorescence area at the same time as the emission of the ultraviolet light is started from the light source 40. Therefore, the image acquiring unit 62 acquires with the image sensor 50, during one clock from when the light source 40 is turned on (t=0 to t=2), the line data for one line forming the fluorescence area image. Moreover, the image acquiring unit 62 acquires with the image sensor 50, during the second one clock from when the fluorescent light disappeared (t=t2 to t=t3), the line data for one line forming the phosphorescence area image.

While the paper sheet 100 is transported for the distance of 1.5 mm in one cycle equivalent to six clocks, the lighting on and off of the light source 40 is controlled and the line data to generate the fluorescence area image is acquired during the first clock, and the line data to generate the phosphorescence area image is acquired during the second clock. Thereafter, during the third clock to the sixth clock, a standby state is maintained in which controlling of the light source and acquisition of the line data are not performed.

The fluorescence and phosphorescence detecting unit 10 refers to the paper sheet data 71 stored in the memory 70 based on the type determination result of the paper sheet 100 received from the paper-sheet type determining unit 20, and recognizes the positions, the shapes, and the like of the fluorescence area and the phosphorescence area on the paper sheet 100. While the fluorescence area passes the measurement area of the image sensor 50, the image acquiring unit 62 repeats the control shown in FIG. 5 in accordance with the transport timing of the paper sheet 100 by the paper sheet transport unit 30, and acquires the line data line-by-line to generate the fluorescence area image. Similarly, the image acquiring unit 62 repeats the control shown in FIG. 5 while the phosphorescence area passes the measurement area by the image sensor 50, and acquires the line data line-by-line to generate the phosphorescence area image.

Specifically, by repeating the light source control shown in (b) of FIG. 5 and the acquisition of the line data shown in (f) of FIG. 5, while the paper sheet 100 transported by the paper sheet transport unit 30 passes the measurement area by the image sensor 50, both the fluorescence image 201 and the phosphorescence image 301 shown in FIG. 1B can be acquired simultaneously.

In this manner, while the paper sheet 100 transported at a high speed by the paper sheet transport unit 30 passes through the fluorescence and phosphorescence detecting unit 10, both the fluorescence image obtained by capturing the fluorescent light and the phosphorescence image obtained by capturing the phosphorescent light can be acquired in the fluorescence and phosphorescence detecting unit 10. Moreover, because the fluorescence and phosphorescence detecting unit 10 includes the sensor units 151 and 251 arranged above and below across the transport path, while the paper sheet 100 transported at a high speed by the paper sheet transport unit 30 passes through the fluorescence and phosphorescence detecting unit 10, the fluorescence image and the phosphorescence image of the front side of the paper sheet 100 and the fluorescence image and the phosphorescence image of the back side of the paper sheet 100 can be acquired simultaneously.

Because the reading of the image data for generating the fluorescence image and the phosphorescence image can be conducted during the two clocks as shown in FIG. 5, the reading of the image data can be performed at a minimal pitch of 0.5 mm by controlling the operation of the light source 40 and the image sensor 50. Moreover, if the reading of the image data is performed in a serial manner in the upper and lower sensor units 151 and 251 during one cycle of 1.5 mm shown in FIG. 5, the reading of the image data can even be performed at a 3.0 mm pitch. That is, in the fluorescence and phosphorescence detecting unit 10 according to the present embodiment, the image data for generating the fluorescence image and the phosphorescence image can be acquired at a pitch between 0.5 mm and 3.0 mm. When this reading pitch is converted into time, it will be 250 µs to 1.5 ms. The reading pitch (time) of the image data, is determined, between 0.5 mm to 3.0 mm (250 µs to 1.5 ms), based on a persistence characteristic of the phosphorescence ink used on the paper sheet 100 namely the emission characteristic of the phosphorescent light.

One of advantages of the fluorescence and phosphorescence detecting unit 10 is that it can detect with a high precision a phosphorescent light having weak emission intensity. This point is explained below. Because the upper sensor unit 151 and the lower sensor unit 251 of the fluorescence and phosphorescence detecting unit 10 have the same configuration, the explanation is given by taking the upper sensor unit 151 as an example.

Figure 6:
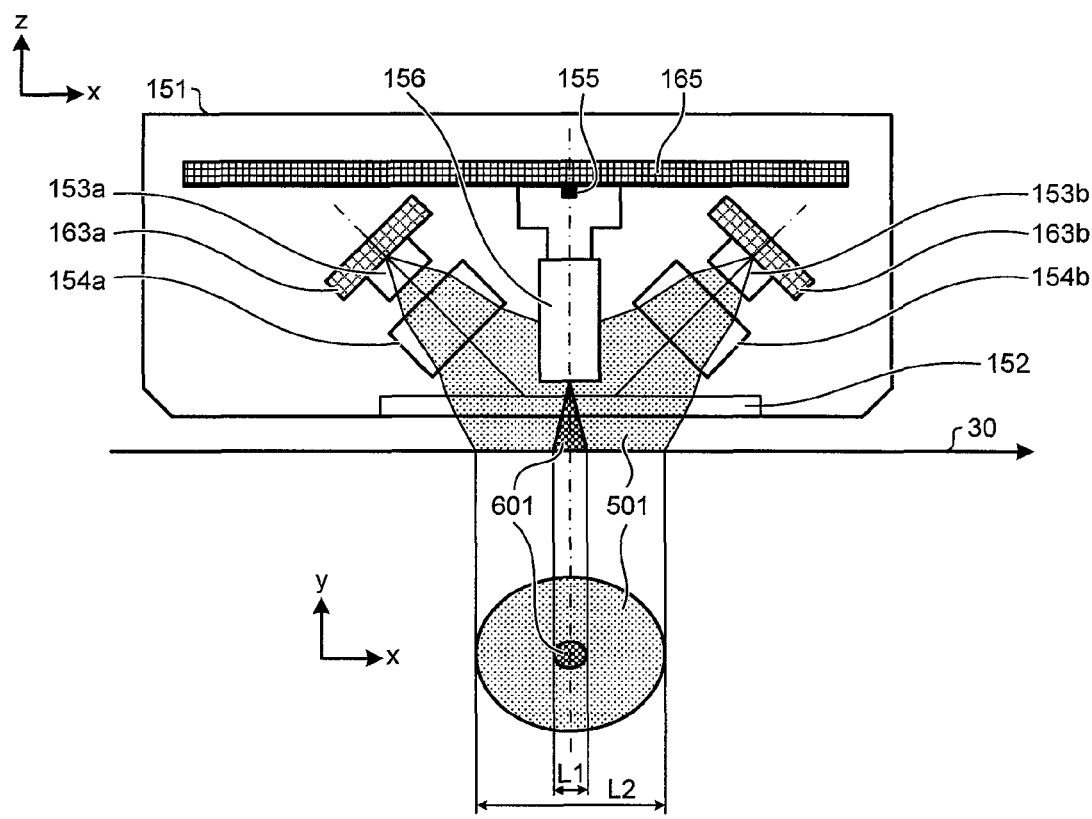
FIG. 6 is a schematic diagram for explaining an emission range of an excitation light and a measurement area of image data by the fluorescence and phosphorescence detecting unit.

FIG. 6 is a schematic diagram for explaining an emission area 501 of the excitation light and a measurement area 601 of the image data by the fluorescence and phosphorescence detecting unit 10. An upper part of FIG. 6 shows schematic cross-sectional view of the sensor unit 151 viewed from a side. A lower part of FIG. 6 shows a schematic diagram of the emission area 501 of the excitation light emitted by the sensor unit 151 and the measurement area 601 of the image data viewed from above.

When the light source 40 is controlled by the light-source control unit 61 and the ultraviolet LEDs 153a and 153b are turned on, as shown in FIG. 6, the emission area 501 of the ultraviolet light that has passed through the visible light cut-off filters 154a and 154b will be elliptical with the long axis thereof having a length of L2 on the transport path on which the paper sheet 100 is transported by the paper sheet transport unit 30. Moreover, the measurement area from which the image acquiring unit 62 acquires the image data of the paper sheet 100 by using the light receiving element 155 is the same area from which the rod lens array 156 receives the reflected light from the paper sheet 100. Specifically, as shown in FIG. 6, the measurement area 601 will be elliptical with the long axis thereof having a length of L1 on the paper sheet 100 transported by the paper sheet transport unit 30. In the present embodiment, to simplify the explanation, only one set of structure including the ultraviolet LEDs 153a and 153b, the rod lens array 156, and the like are shown in the figure; however, similar structures are arranged in an array in the Y-axis direction in a real apparatus. Therefore, for example, the emission area 501 and the measurement area 601 shown in FIG. 6 continue along the Y-axis direction with a partial overlap between adjacent emission areas 501 and measurement areas 601 respectively. With this configuration, data can be acquired from the entire surface of the paper sheet 100 when the paper sheet 100 passes the position of the sensor unit 151.

In the fluorescence and phosphorescence detecting unit 10, the emission area 501 of the excitation light is set wide to avoid a situation that the phosphorescence area in which the phosphorescent light is excited on the paper sheet 100 moves and goes out of the measurement area 601 for acquiring the image data while the image data of the phosphorescent light is being acquired.

Figure 7:
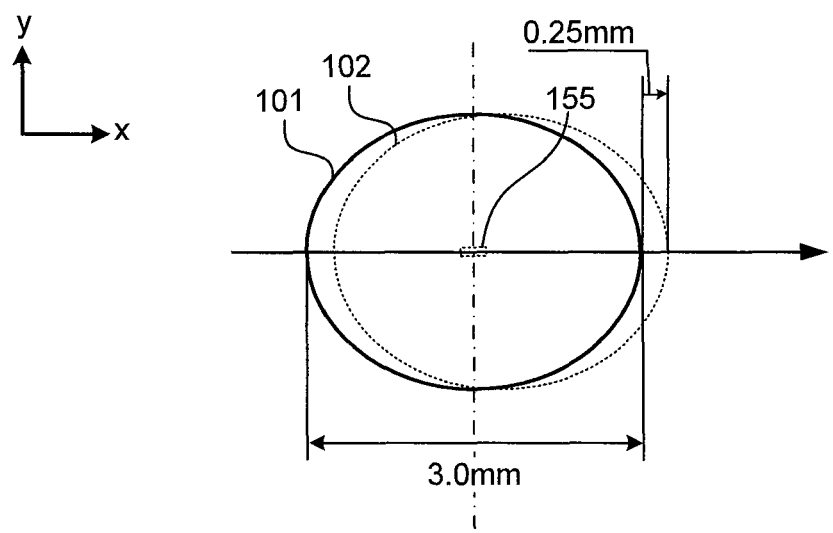
FIG. 7 is a view indicating a movement of a partial area of the paper sheet corresponding to the emission range of the excitation light.

FIG. 7 is a view indicating a movement of a partial area 101 of the paper sheet 100 corresponding to the emission area 501 of the excitation light. The emission area 501 of the excitation light by the fluorescence and phosphorescence detecting unit 10 is elliptical with the length L2 of the long axis being 3.0 mm. If a phosphorescence material is present in the partial area 101 of the paper sheet 100 corresponding to this emission area 501, a phosphorescent light will be excited from this partial area 101.

Figure 8:
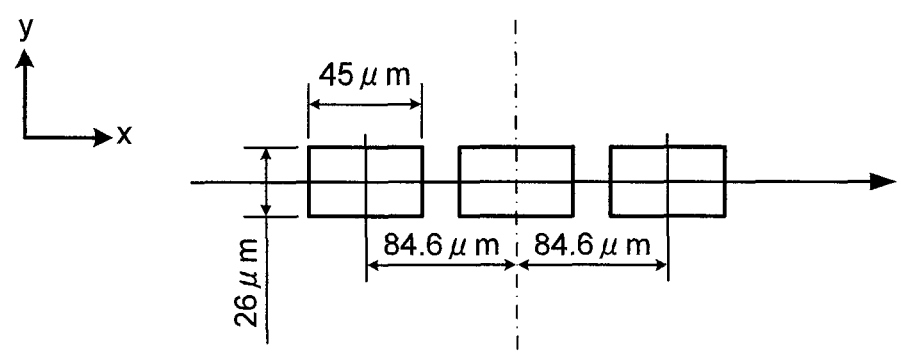
FIG. 8 is a view for explaining a layout of light receiving elements.

As shown with a dashed-line rectangle in FIG. 7, the position corresponding to the light receiving element 155 of the sensor unit 151 is the center of the partial area 101. FIG. 8 is an enlarged view of the light receiving elements 155 shown in FIG. 7. FIG. 8 shows a layout of the light receiving elements 155. Because of the small size of the light receiving element 155, it is not shown in FIGS. 4 and 6; however, as mentioned above, the light receiving elements 155 are arranged in three rows. Specifically, as shown in FIG. 8, each of the light receiving elements of the RGB having a light receiving surface of a length of 45 µm in the X-axis direction and a width of 26 µm in the Y-axis direction is arranged in three rows with a center-to-center distance of 84.6 µm.

In the fluorescence and phosphorescence detecting unit 10, as shown in FIG. 5, the line data of the phosphorescence area image is acquired after the light source 40 is turned off. The paper sheet 100 transported at the speed of 2000 mm/s moves for 0.25 mm during one clock in which the line data for one line of the phosphorescence image is acquired. Therefore, the partial area 101 on the paper sheet 100 shown with a solid line in FIG. 7 moves for 0.25 mm in the transport direction to a partial area 102 shown with a dashed line; however, the distance 0.25 mm is smaller than the length L2, i.e., 3.0 mm, of the long axis of the partial area 101 (102) from which the phosphorescent light is excited. Moreover, because the line data of the phosphorescent light is acquired from a substantially central area of the partial area 101 (the emission area 501 shown in FIG. 6) in which the excitation light is emitted, i.e., from a sufficiently smaller area (the measurement area 601 shown in FIG. 6) in comparison to the partial area 101, it is possible to detect the phosphorescent light with a high precision without being affected by the movement of the partial area 101.

In this manner, in the fluorescence and phosphorescence detecting unit 10, the phosphorescent light can be detected with a high precision because the length (L2=3.0 mm) of the long axis of the emission area 501 of the excitation light of the light source 40 is set 10 times or more of the distance (0.25 mm) for which the paper sheet 100 moves in one clock in which the line data of one line of the phosphorescence image is acquired.

Moreover, in the fluorescence and phosphorescence detecting unit 10, the measurement area 601 of the image data is set wide to prevent a situation that, while the image data of the phosphorescent light is being acquired, the partial area of the paper sheet 100 from which the data is being acquired moves and goes completely out of the measurement area 601 from which the image data is acquired. That is, the partial area of the paper sheet 100 corresponding to the measurement area 601 is not allowed to move outside of the measurement area 601 during the measurement.

Specifically, in the fluorescence and phosphorescence detecting unit 10 according to the present embodiment, even if the measurement area 601 changes due to moving up and down variation of the paper sheet 100 that is transported on the transport path, it is set that the length L1 of the long axis of the measurement area 601 is 0.43 mm or more by use of the rod lens array 156 having an aperture angle of 20 degrees. That is, even if the measurement area 601 is the narrowest, the distance (0.25 mm) for which the paper sheet 100 moves during one clock for measuring the line data of one line of the phosphorescent light is suppressed to be 60% or lower of the length (L1=0.43 mm) of the long axis of the measurement area 601. As a result, the phosphorescent light can be detected with a high precision because a situation, in which the paper sheet 100 is transported while the line data of one line is being acquired and the partial area of the paper sheet 100 that is being measured goes completely out of the measurement area 601 and the line data of a completely different partial area is acquired, is prevented.

In the fluorescence and phosphorescence detecting unit 10, because the rod lens array 156 having the aperture angle of 20 degrees is used to secure the measurement area 601 having the length L1=0.43 mm or more of the long axis irrespective of the transport state of the paper sheet 100 transported by the paper sheet transport unit 30, a brighter image can be acquired as compared to a case in which the aperture angle is small. Specifically, an image that is four times brighter than an image acquired when the aperture angle is 12 degrees can be acquired when the aperture angle is 20 degrees. Therefore, the light source that includes an LED array is used in the present embodiment; however, a light source having less number of the LEDs and a light guide can be used.

As mentioned above, with the fluorescence and phosphorescence detecting unit 10 according to the present embodiment, the fluorescence image, the phosphorescence image, and the subtraction image generated from the fluorescence image and the phosphorescence image can be acquired from the paper sheet 100. When obtaining the subtraction image of the fluorescence image and the phosphorescence image, an image indicating the feature of the phosphorescent light can be obtained by performing the gain correction of the phosphorescence image. Moreover, the gain correction corresponding to the type of the phosphorescent light can be performed by using a coefficient set previously for each area from which the phosphorescent light is excited on the paper sheet 100.

Moreover, in the fluorescence and phosphorescence detecting unit 10, because the emission area 501 on the paper sheet 100 in which the excitation light is emitted by the light source 40 and the measurement area 601 in which the line data to generate the phosphorescence image is acquired from the paper sheet 100 are set wide, the image data of the phosphorescent light can be acquired with a high precision from the paper sheet 100 that is transported at a high speed.

Moreover, because the fluorescence and phosphorescence detecting unit 10 includes two sensor units 151 and 251 that are installed so as to sandwich the transport path from above and below, the fluorescence image and the phosphorescence image can be acquired from both the sides of the paper sheet 100 that is transported at a high speed. Moreover, because the image sensors 50 in the sensor units 151 and 251, which are arranged above and below opposing each other, are arranged by displacing in the transport direction, the fluorescence image and the phosphorescence image can be acquired with a high precision as the images are not affected by the excitation lights emitted from the opposing light sources 40 of the sensor units 151 and 251 that are arranged across the transport path.

INDUSTRIAL APPLICABILITY

As explained above, the fluorescence and phosphorescence detecting apparatus according to the present invention is useful in detecting the fluorescent light and the phosphorescent light with a high precision by aiming to acquire the feature amount of the fluorescent light and the phosphorescent light of the paper sheet as one type of the data that can be used to determine the authenticity of the paper sheet.

EXPLANATION OF REFERENCE NUMERALS

10 Fluorescence and phosphorescence detecting unit
20 Paper-sheet type determining unit
30 Paper sheet transport unit
40 Light source
50 Image sensor
60 Control unit
61 Light-source control unit
62 Image acquiring unit
63 Image processing unit
64 Image output unit
70 Memory
151, 251 Sensor unit
152, 252 Transparent member
153a, 153b, 253a, 253b LED
154a, 154b, 254a, 254b Visible light cut-off filter
155, 255 Photodetecting element
156, 256 Rod lens array
165, 265, 163a, 163b, 263a, 263b Substrate

The invention claimed is:

1. A fluorescence and phosphorescence detecting apparatus that detects both a fluorescent light and a phosphorescent light emitted from a paper sheet that is being transported on a transport path, comprising:
    a sensor unit including
        a light source that emits light on the paper sheet;
        an image sensor that detects the fluorescent light and the phosphorescent light excited on the paper sheet by irradiation of the light; and
        a light receiving lens that guides the fluorescent light and the phosphorescent light excited on the paper sheet to the image sensor, wherein
    the data of the fluorescent light is acquired while the light source emits the light on the paper sheet, and the data of the phosphorescent light is acquired after emission of the light is stopped.

2. The fluorescence and phosphorescence detecting apparatus as claimed in claim 1, wherein
    the light is ultraviolet light, and
    the sensor unit further includes
    a visible light cut-off filter arranged between the light source and the transport path; and
    an ultraviolet light cut-off filter arranged between the transport path and the image sensor, and
    the image sensor obtains a color image.

3. The fluorescence and phosphorescence detecting apparatus as claimed in claim 1, wherein the sensor unit further includes an image processing unit that corrects a gain of a phosphorescence image obtained by capturing the phosphorescent light by the image sensor, by using a coefficient set previously.

4. The fluorescence and phosphorescence detecting apparatus as claimed in claim 3, wherein the coefficient is a reciprocal number of a decay rate of the phosphorescent light.

5. The fluorescence and phosphorescence detecting apparatus as claimed in claim 3, wherein the coefficient is respectively set for each type and for each direction of the paper sheet.

6. The fluorescence and phosphorescence detecting apparatus as claimed in claim 3, wherein the coefficient is respectively set for each area of the paper sheet from which the phosphorescent light is excited.

7. The fluorescence and phosphorescence detecting apparatus as claimed in claim 3, wherein the coefficient is respectively set for each color of the phosphorescent light.

8. The fluorescence and phosphorescence detecting apparatus as claimed in claim 3, wherein the image processing unit generates a subtraction image from a gain corrected phosphorescence image and a fluorescence image obtained by capturing the fluorescent light by the image sensor.

9. The fluorescence and phosphorescence detecting apparatus as claimed in claim 8, wherein the image processing unit corrects the gain of the phosphorescence image to generate the subtraction image, the subtraction image is generated by removing an image of an area in which both the fluorescent light and the phosphorescent light are excited.

10. The fluorescence and phosphorescence detecting apparatus as claimed in claim 1, wherein the image sensor can acquire image data of the fluorescent light and the phosphorescent light at a pitch between 0.5 mm and 3.0 mm.

11. The fluorescence and phosphorescence detecting apparatus as claimed in claim 1, wherein the light source emits the light on an area of the paper sheet being transported on the transport path, and the data of the phosphorescent light and the data of the fluorescent light are acquired from the area of the paper sheet.

12. The fluorescence and phosphorescence detecting apparatus as claimed in claim 1, wherein
    two sensor units are arranged above and below the transport path and opposing each other across the transport path, and image sensors in the two sensor units are off-set along a transport direction of the transport path, and
    one of the two sensor units detects the fluorescent light and the phosphorescent light of an upper surface of the paper sheet, and the other of the two sensor units detects the fluorescent light and the phosphorescent light of a lower surface of the paper sheet.

* * * * *